(12) United States Patent
Tilt et al.

(10) Patent No.: US 12,201,394 B2
(45) Date of Patent: Jan. 21, 2025

(54) APPARATUS AND METHOD FOR PROTECTING AN OPERATING FIELD

(71) Applicant: MEDSTAR HEALTH, INC., Columbia, MD (US)

(72) Inventors: Alexandra Tilt, Columbia, MD (US); Pamela Tan, Columbia, MD (US)

(73) Assignee: MEDSTAR HEALTH, INC., Columbia, MD (US)

( * ) Notice: Subject to any disclaimer, the term of this patent is extended or adjusted under 35 U.S.C. 154(b) by 0 days.

(21) Appl. No.: 18/301,831

(22) Filed: Apr. 17, 2023

(65) Prior Publication Data

US 2023/0248458 A1    Aug. 10, 2023

Related U.S. Application Data

(63) Continuation of application No. 16/884,424, filed on May 27, 2020, now Pat. No. 11,648,077.

(60) Provisional application No. 62/853,979, filed on May 29, 2019.

(51) Int. Cl.
*A61B 46/00* (2016.01)
*A61B 46/20* (2016.01)
*A45D 8/02* (2006.01)
*A45D 8/12* (2006.01)

(52) U.S. Cl.
CPC .............. *A61B 46/20* (2016.02); *A61B 46/40* (2016.02); *A45D 8/02* (2013.01); *A45D 8/12* (2013.01); *A61B 2046/205* (2016.02)

(58) Field of Classification Search
CPC ... A61B 46/20; A61B 2046/201; A61B 46/40; A45D 8/02; A45D 8/12; A45D 19/0066; A45D 19/0075; A45D 19/0083; A45D 19/14; A45D 19/18; A42B 1/012;
(Continued)

(56) References Cited

U.S. PATENT DOCUMENTS 1,997,063 A    4/1935  Hughes
2,791,778 A *  5/1957  Wardley ................. A45D 44/08
                                                2/174
(Continued)

FOREIGN PATENT DOCUMENTS

AU    2013 337 891 B2    5/2014
CN       204618408 U     9/2015
(Continued)

OTHER PUBLICATIONS

PCT International Search Report and Written Opinion for corresponding International Application Serial No. PCT/US2020/034645, mailed Sep. 4, 2020, pp. 1-13.

*Primary Examiner* — Camtu T Nguyen
(74) *Attorney, Agent, or Firm* — ArentFox Schiff LLP

(57) ABSTRACT

An apparatus for protecting an operating field. The apparatus includes a sheet configured to cover a patient's hair during an operation. A sealing member is provided on or joined to a leading end of the sheet. The sealing member is configured to be applied to a patient's skin adjacent to an operating field to create a seal between the operating field and the patient's hair. At least one anchoring member is joined to the sheet adjacent to the leading end of the sheet. The at least one anchoring member is configured to be attached to the patient's hair adjacent to the operating field to anchor the apparatus to the patient.

10 Claims, 9 Drawing Sheets

(58) Field of Classification Search
CPC ........... A42B 1/017; A42B 1/018; A42B 1/04; A42B 1/18; A42B 1/00; A42B 5/00
See application file for complete search history.

(56) References Cited

U.S. PATENT DOCUMENTS

| | | | | |
|---|---|---|---|---|
| 3,952,738 | A * | 4/1976 | Krzewinski | A61B 46/00 128/855 |
| 3,955,569 | A | 5/1976 | Krzewinski et al. | |
| 4,457,026 | A * | 7/1984 | Morris | A61B 46/00 2/114 |
| 4,572,173 | A | 2/1986 | Comeau | |
| 4,605,017 | A * | 8/1986 | Thompson | A45D 19/18 132/333 |
| 5,248,307 | A * | 9/1993 | Sokoloff | A61B 46/10 604/327 |
| 5,533,989 | A | 7/1996 | Sokoloff | |
| 5,778,889 | A * | 7/1998 | Jascomb | A61B 46/00 128/853 |
| 5,950,636 | A | 9/1999 | Hickey | |
| 10,342,627 | B2 * | 7/2019 | Esquivel | A61B 46/00 |
| 2019/0116953 | A1 * | 4/2019 | Daly | A45D 19/18 |
| 2021/0106113 | A1 * | 4/2021 | Lee | A42B 1/012 |

FOREIGN PATENT DOCUMENTS

| | | | |
|---|---|---|---|
| GB | 1221547 | A | 2/1971 |
| JP | H0847499 | A | 2/1996 |
| JP | 3071598 | U | 9/2000 |
| JP | 2000517215 | A | 12/2000 |
| WO | 2014/070922 | A1 | 5/2014 |
| WO | 2015/117193 | A1 | 8/2015 |

* cited by examiner

APPARATUS AND METHOD FOR PROTECTING AN OPERATING FIELD

RELATED APPLICATION

The present application is a continuation of U.S. application Ser. No. 16/884,424, filed May 27, 2020, which claims priority from U.S. Provisional Application No. 62/853,979, filed May 29, 2019, the subject matter of both of which are incorporated herein by reference in their entirety.

TECHNICAL FIELD

This disclosure relates to an apparatus and method for protecting an operating field.

BACKGROUND

Sterile draping for surgeries performed on hair-bearing areas of the scalp can be a challenge for users, such as plastic surgeons, head & neck surgeons, and neurosurgeons. Hair in the surgical field may pose an infection risk and may also hinder the user's ability to operate by becoming entangled in the wound and suture material. One common solution to hair in the surgical field involves completely shaving the operative area; indeed, for any surgical procedure elsewhere on the body, hair is commonly shaved using electric clippers at the beginning of the case. However, shaving the scalp is quite noticeable, especially for patients with longer hair, and can have negative psychosocial consequences for many patients. It can be particularly undesirable for female patients undergoing elective cosmetic surgery, such as a face lift, or for children undergoing procedures on the scalp.

As such, users generally proceed with scalp or facial surgery by shaving what they perceive to be a minimal amount of hair necessary to make an incision, and using various techniques to keep unshaved, longer hair out of the sterile surgical field. Some of these techniques include bundling and/or braiding the unshaved hair and securing the bundled or braided hair with a band or clamp. Each these techniques may be inexpensive, readily available, and may decrease procedure time at the end of the case by minimizing postoperative washing and combing of the patient's hair. However, these techniques consume time at the beginning of a procedure while the patient is under anesthesia, which for cosmetic procedures is billable to the patient by the minute. Moreover, many users simply do not have the desire or ability to braid or bundle hair.

Another technique to keep unshaved, longer hair out of the sterile surgical field is to staple surgical drapes to the patient in place at the operating field. This technique is quick, cheap, and readily accessible. However, this technique requires many staples in the patient's scalp that must later be removed and may leave small scars. Another technique is to completely wrap the head of a patient with a drape and secure the patient's hair beneath the drape. This technique is only useful, though, for procedures involving the forehead or ears and cannot be applied to operating fields within the scalp area.

In spite of hair in the operating field frustrating users, there is very little literature devoted to this problem, and the solutions that have been proposed are mediocre at best. This is particularly surprising in an age when surgical drapes have become very specialized and expensive. Surgical facilities spend hundreds of dollars on drapes for every case—all to ensure sterility for the patient and convenience for the user. Therefore, it may be desirable to provide a drape specialized to keep unshaved hair out of the operating field.

SUMMARY

In an aspect, an apparatus for helping to protect a patient's hair is provided. The apparatus includes a sheet configured to cover a patient's hair during an operation. A sealing member is provided on or joined to a leading end of the sheet. The sealing member is configured to be applied to a patient's skin adjacent to an operating field to create a seal between the operating field and the patient's hair. At least one anchoring member is joined to the sheet adjacent to the leading end of the sheet. The at least one anchoring member is configured to be attached to the patient's hair adjacent to the operating field to anchor the apparatus to the patient.

In an aspect, a method for helping to protect a patient's hair is provided. The method includes providing an apparatus for helping to protect a patient's hair. The apparatus is anchored to the patient by attaching at least one anchoring member of the apparatus to the patient's hair adjacent to an operating field. A seal is created between the operating field and the patient's hair by applying a sealing member of the apparatus to the patient's skin adjacent to the operating field. The patient's hair adjacent to the operating field is covered with a sheet of the apparatus.

BRIEF DESCRIPTION OF THE DRAWINGS

For a better understanding, reference may be made to the accompanying drawings, in which.

DESCRIPTION OF ASPECTS OF THE DISCLOSURE

Figure 1:
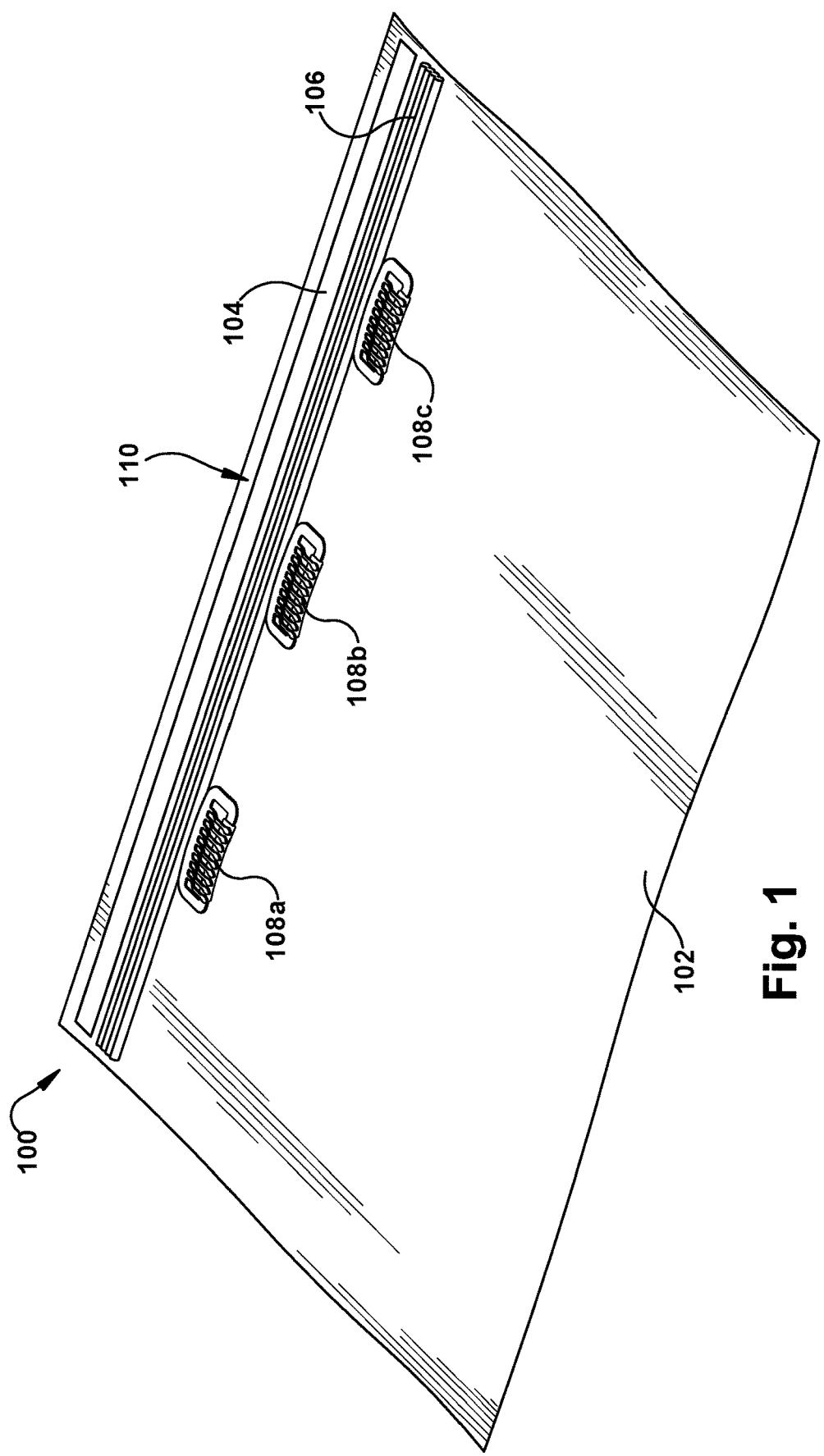
FIG. 1 is a bottom view of a specialized drape according to one configuration.

Unless defined otherwise, all technical and scientific terms used herein have the same meaning as is commonly understood by one of skill in the art to which the present disclosure pertains.

As used herein, the term "patient" can refer to any warm-blooded organism including, but not limited to, human beings, pigs, rats, mice, dogs, goats, sheep, horses, monkeys, apes, rabbits, cattle, farm animals, livestock, etc.

As used herein, the term "user" can be used interchangeably to refer to an individual who prepares for, assists with, and/or performs a procedure.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "contacting," etc., another element, it can be directly on, attached to or contacting the other element or intervening elements may also be present. It will also be appreciated by those of skill in the art that references to a structure or feature that is disposed "adjacent" another feature may not have portions that overlap or underlie the adjacent feature.

Spatially relative terms, such as "over" and the like, may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures. For example, if a device in the Figures is inverted, elements described as "over" or "on top of" other elements or features would then be oriented "under" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 2:
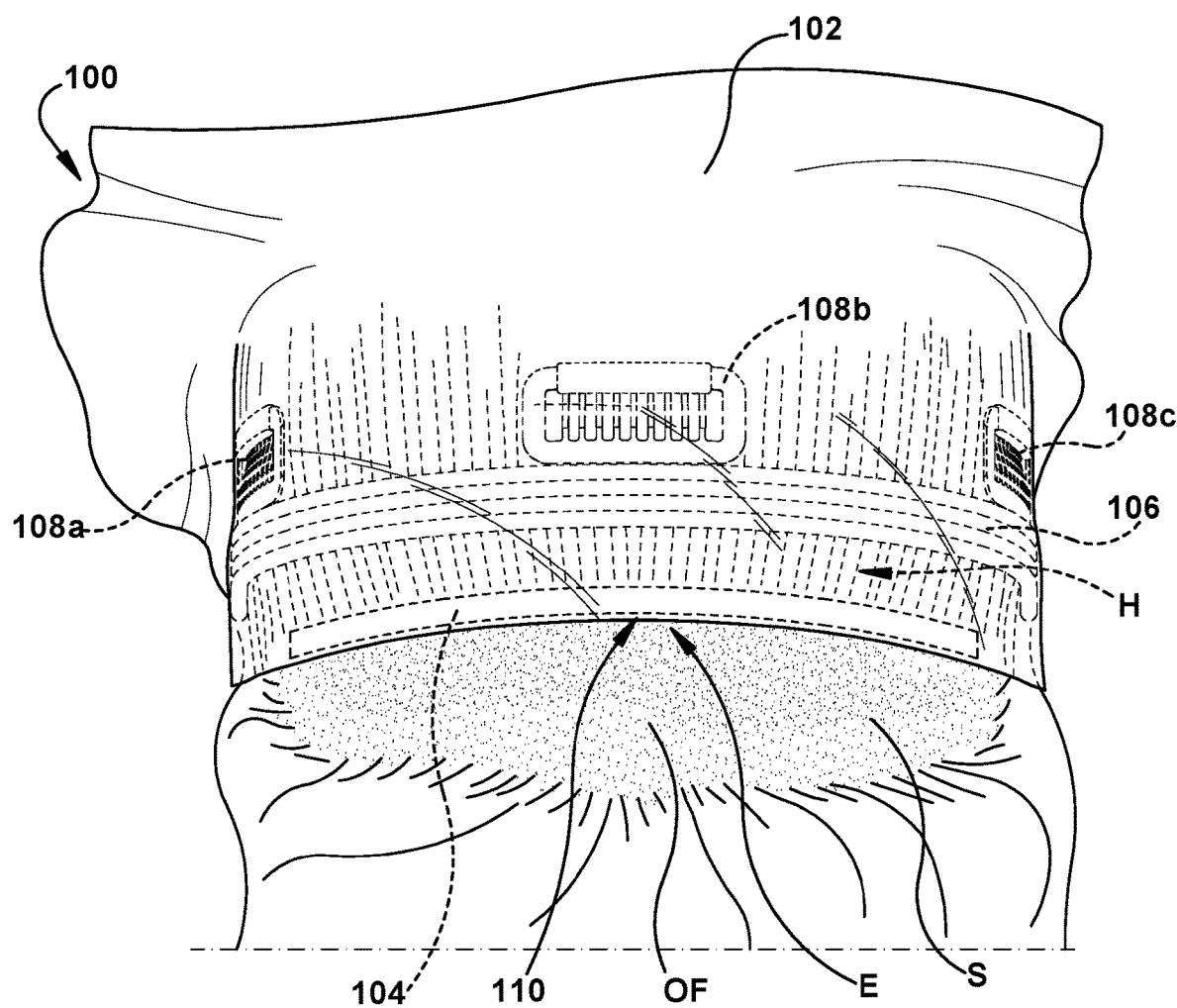
FIG. 2 illustrates the specialized drape of FIG. 1 in a first example use environment.

FIGS. 1-2 depict a first configuration of a specialized drape 100 for helping to prevent a patient's hair from entering an operating field during procedures involving the patient's scalp, forehead, ears, and/or neck. The specialized drape 100 may include a sheet 102, a sealing member 104, a hair guiding member 106, and at least one anchoring member 108 (shown here as anchoring members 108a, 108b, 108c). The sheet 102 may be at least partially translucent and/or transparent so, if overlying the face, an anesthesiologist, for example, can monitor endotracheal tube placement throughout a procedure. The sheet 102 may also be formed from an impervious material that may help to protect the patient's hair H and/or skin S outside of the operating field OF from the byproducts of surgery (FIG. 2). The sheet 102 may be sterile or non-sterile, depending on the procedure.

The sealing member 104 may be incorporated within, provided on, and/or attached to the sheet 102 at or adjacent to a leading end 110 of the sheet 102. The sealing member 104 is configured to help separate the operating field OF from the patient's hair H and/or skin S outside of the operating field OF (FIG. 2). The sealing member 104 may be an adhesive, glue, resilient strip (e.g., silicone), or any other desired barrier that can be configured to separate the operating field OF from the patient's hair. In the example configuration shown in FIG. 1, the sealing member is an adhesive provided on the leading end 110 of the sheet 102. A removable protective strip (not shown) may cover the adhesive sealing member 104 prior to use. The sealing member 104 may be a hydrocolloid adhesive. The hydrocolloid adhesive may allow for better contact and seal around concave and circular surfaces that may contain small stumps of residual hair after shaving with electric clippers than regular tape adhesives. Moreover, the hydrocolloid adhesive may be easier to remove and less likely to cause an adverse skin reaction in patients with sensitive skin than would regular tape adhesives.

Although the sealing member 104 has been described as being provided on the leading end 110 of the sheet 102, it is contemplated that the sealing member 104, such as a glue-based sealing member 104, may be first provided on the patient's skin S instead of on the leading end 110 of the sheet 102. Once provided on the patient's skin, the leading end 110 of the sheet 102 may be pressed onto the sealing member 104 to join the sealing member 104 to the leading end 110 of the sheet 104 and the sheet 104 to the patient.

The hair guiding member 106 is incorporated within, provided on, and/or attached to the sheet 102 adjacent to the leading end 110 of the sheet 102. The hair guiding member 106 may be configured to comb and hold the patient's hair H out of an operating field OF during application of the specialized drape 100 (FIG. 2). The hair guiding member 106 may be at least partially formed from a hook portion and/or a loop portion of a hook-and-loop fastener.

The at least one anchoring member 108 is incorporated within, provided on, and/or attached to the sheet 102 adjacent to the leading end 110 of the sheet 102. The at least one anchoring member 108 may be configured to be attached to the patient's hair H during application of the specialized drape 100. The at least one anchoring member 108, once attached to the patient's hair H, may anchor the specialized drape 100 to the patient and help avoid displacement of the specialized drape 100 during a procedure (FIG. 2). The at least one anchoring member 108 may be a hair clip, a comb, a hairpin, any other fastener suitable for attaching the specialized drape 100 to the patient, or any combination thereof. In the example configuration shown in FIGS. 1-2, the specialized drape 100 includes a plurality of hair clip anchoring members 108 (shown here as hair clip anchoring members 108a, 108b, 108c).

In its packaging, the sheet 102 may be folded on top of the at least one anchoring member 108, and the sealing member 104 may be covered and protected by the removable protective strip. To apply the specialized drape 100 to a patient, a user gently but firmly combs the patient's hair away from an operating field OF with the hair guiding member 106. The at least one anchoring member 108 may be attached to the patient's hair H while and/or after the hair guiding member 106 is used to comb the patient's hair H away from the operating field OF. For example, the at least one anchoring member 108 may be inserted into the patient's hair H and then "snapped" into locking engagement with the patient's hair H through the use of a snap-attachment mechanism of the anchoring member 108.

Once the specialized drape 100 has been secured/anchored to the patient's hair H through the hair guiding member 106 and/or the at least one anchoring member 108, the user removes the protective strip and presses the sealing member 104 onto a shaved area at an edge E of the operating field OF. As shown in FIG. 2, the user then unfolds the sheet 102 over the patient's hair H. At this point, all hair H adjacent to the operating field OF should be covered by the specialized drape 100 and an appropriate seal has been created along the edges E of the operating field OF. The operating field OF may now be prepped and disinfected with, for example, betadine or chlorhexidine, and may be draped with standard sterile adhesive drapes according to usual sterile techniques. Alternatively, the specialized drape 100 may be packaged sterilely and the user may apply the specialized drape 100 as described above and in a sterile fashion once the designated operating field OF has been shaved and disinfected. At the end of surgery, the specialized drape 100 is removed and may be discarded or cleaned and sterilized using known techniques.

The sequence of applying the specialized drape 100 to a patient presented above illustrates just one example sequence of operation. This sequence is not intended to limit the manner in which the specialized drape 100 is applied to a patient. Any of the steps detailed above can be performed before or after any other step depending on the configuration of the of the specialized drape 100 and/or the procedure. For example, when the specialized drape 100 includes a glue-based sealing member 104, it may be desirable to apply the glue-based sealing member 104 to the patient's skin S before attaching the rest of the specialized drape 100 in the manner described above.

The specialized drape 100 may have alternate configurations in order to customize the specialized drape 100 for different procedures. For example, particular configurations of the specialized drape 100 may have more of or less of any of the features discussed above. Further, particular configurations of the specialized drape 100 may require different sizes for each of the features discussed above based on incision requirements for different surgical procedures.

Figure 3:
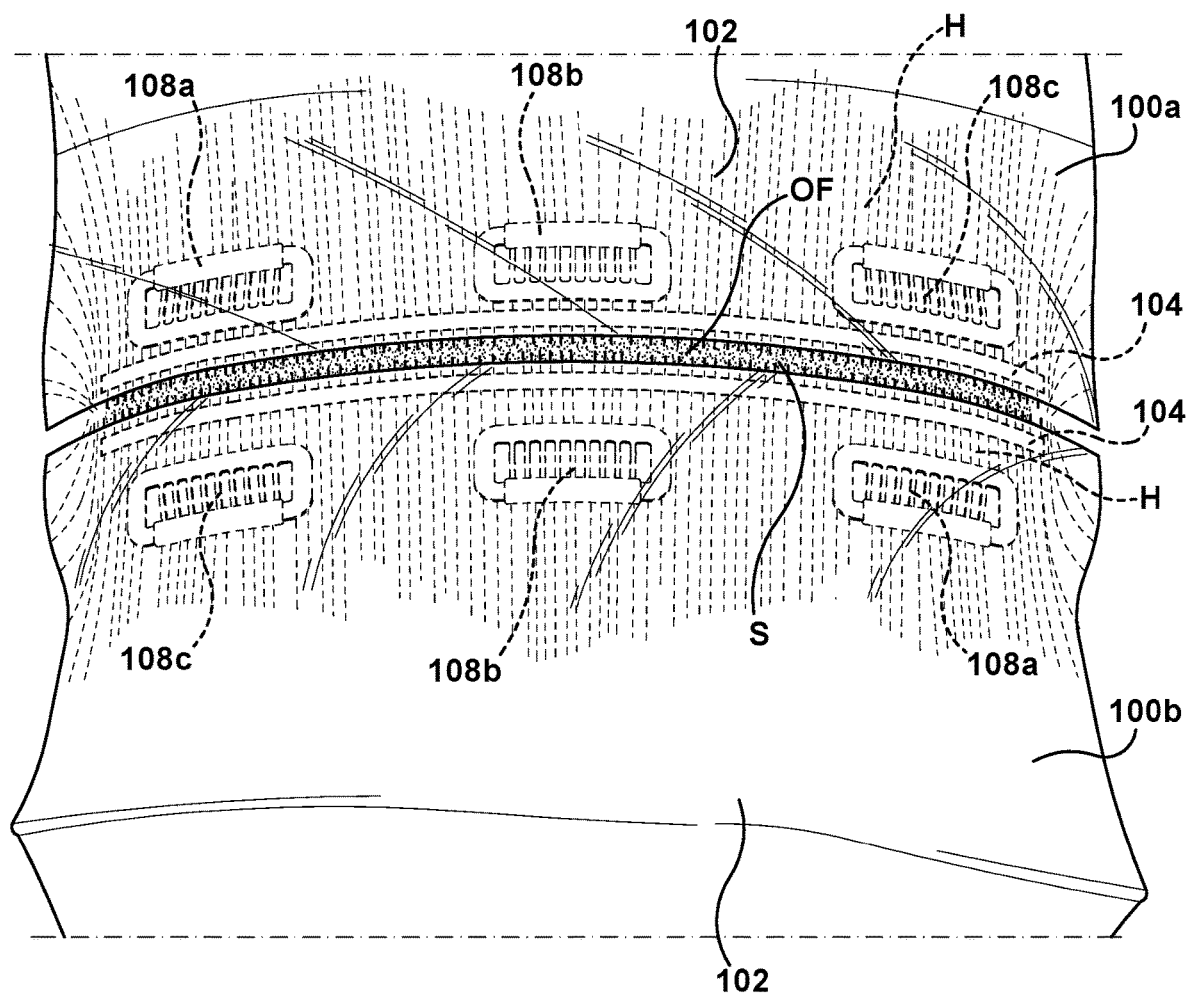
FIG. 3 illustrates the specialized drape of FIG. 1 in a second example use environment.

FIGS. 1-15 depict example alternative configurations for the specialized drape. The configuration shown in FIGS. 1-2 is a substantially linear configuration of the specialized drape 100 that may be particularly well suited for large scalp wounds, such as bicoronal incisions. FIG. 3 shows the use of two linear specialized drapes 100 (shown here as specialized drapes 100a and 100b) on a patient's scalp.

Figure 4:
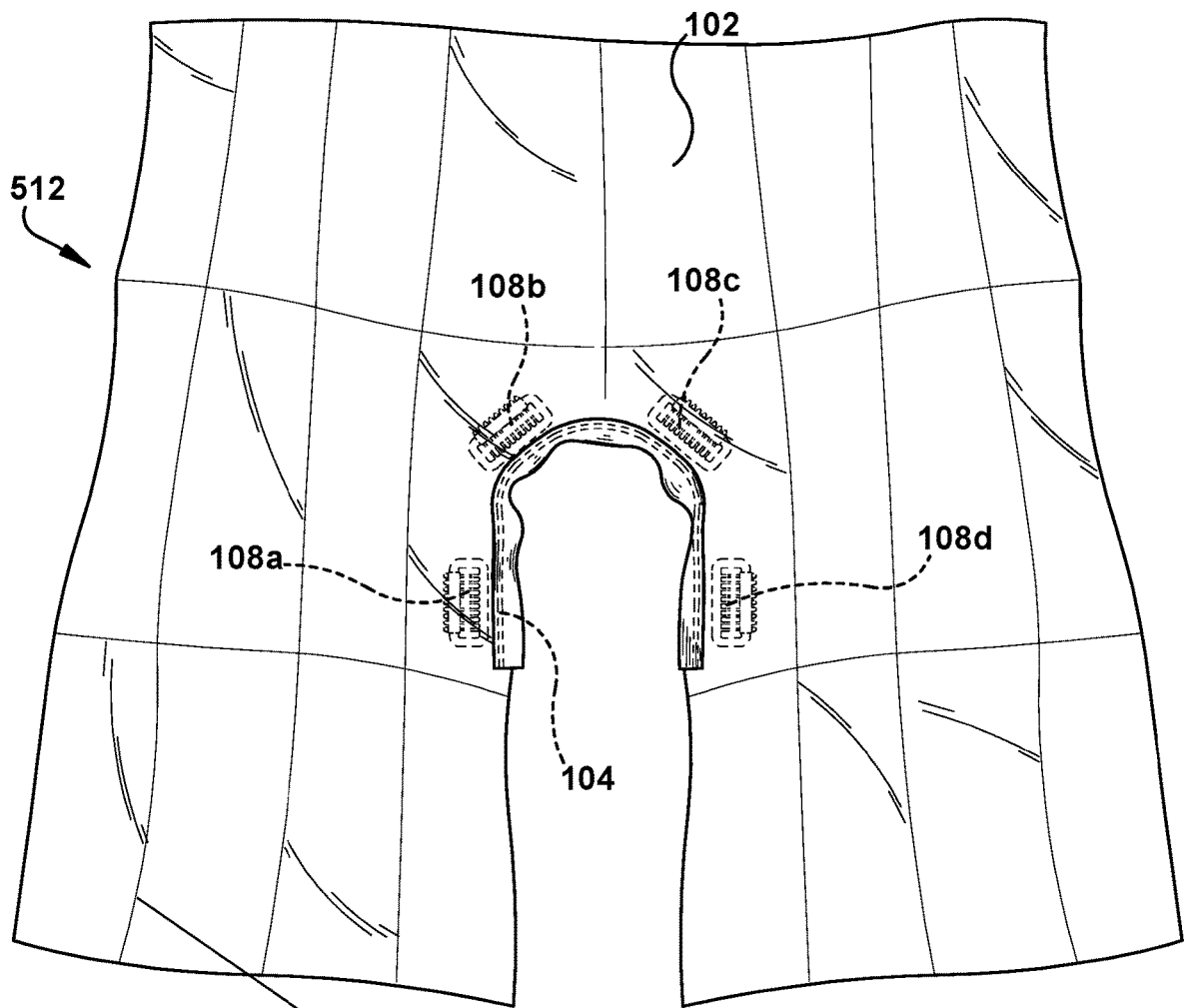
FIG. 4 is a top view of the specialized drape of FIG. 1, in another configuration.
Figure 5:
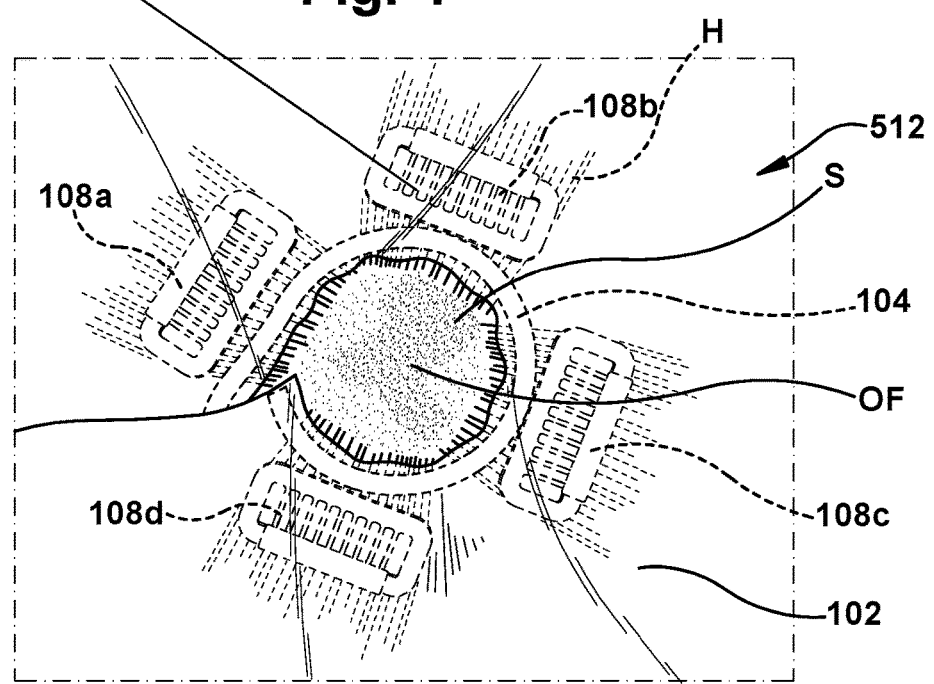
FIG. 5 illustrates the specialized drape of FIG. 4 in a first example use environment.

The configuration shown in FIG. 4 is a specialized drape 512 that has a substantially U-shaped configuration. The U-shaped specialized drape 512 may be flexible and versatile so that a user may use the U-shaped specialized drape 512 as a linear specialized drape, and additionally may use the U-shaped specialized drape as a substantially circular drape. As shown in FIG. 4, the U-shaped specialized drape 512 includes a plurality of hair clip anchoring members 108 (shown here as hair clip anchoring members 108a, 108b, 108c, 108d). Although not shown in FIG. 4, the U-shaped specialized drape 512 may include a hair guiding member 106. FIG. 5 depicts the U-shaped specialized drape 512 being selectively flexed and used as a substantially circular drape. The U-shaped specialized drape 512, when maneuvered into a substantially circular shape, may be particularly well suited for being placed around the circumference of a small incision and/or a small operating field OF for excision of a 1-2 cm lesion of the scalp.

Figure 6:
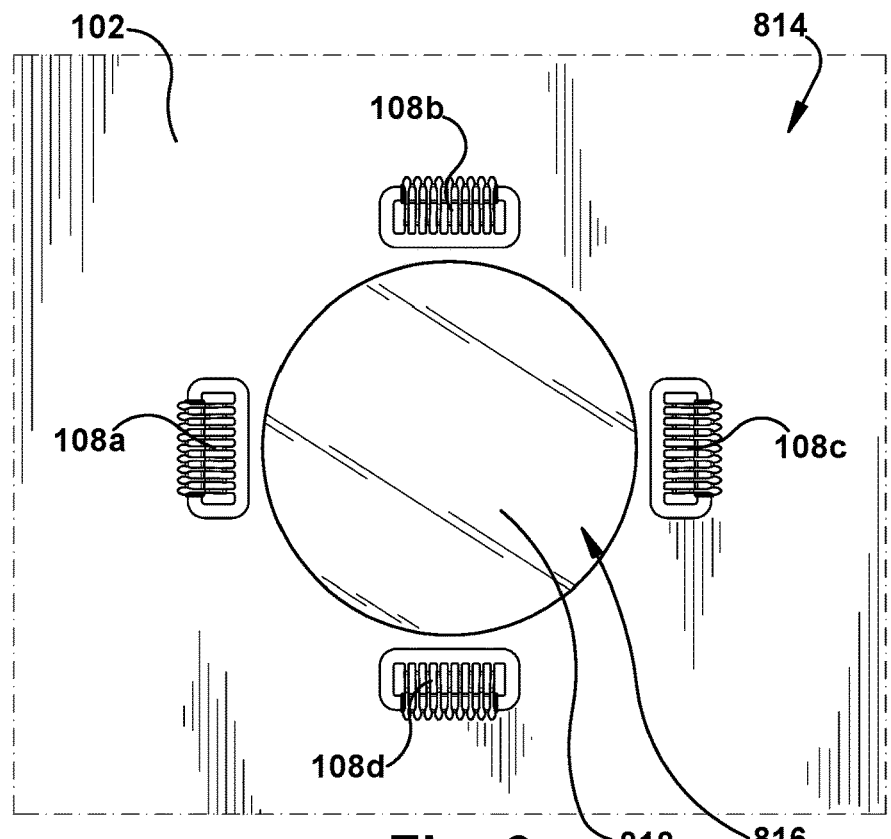
FIG. 6 is a bottom view of a portion of the specialized drape of FIG. 1, in another configuration.
Figure 7:
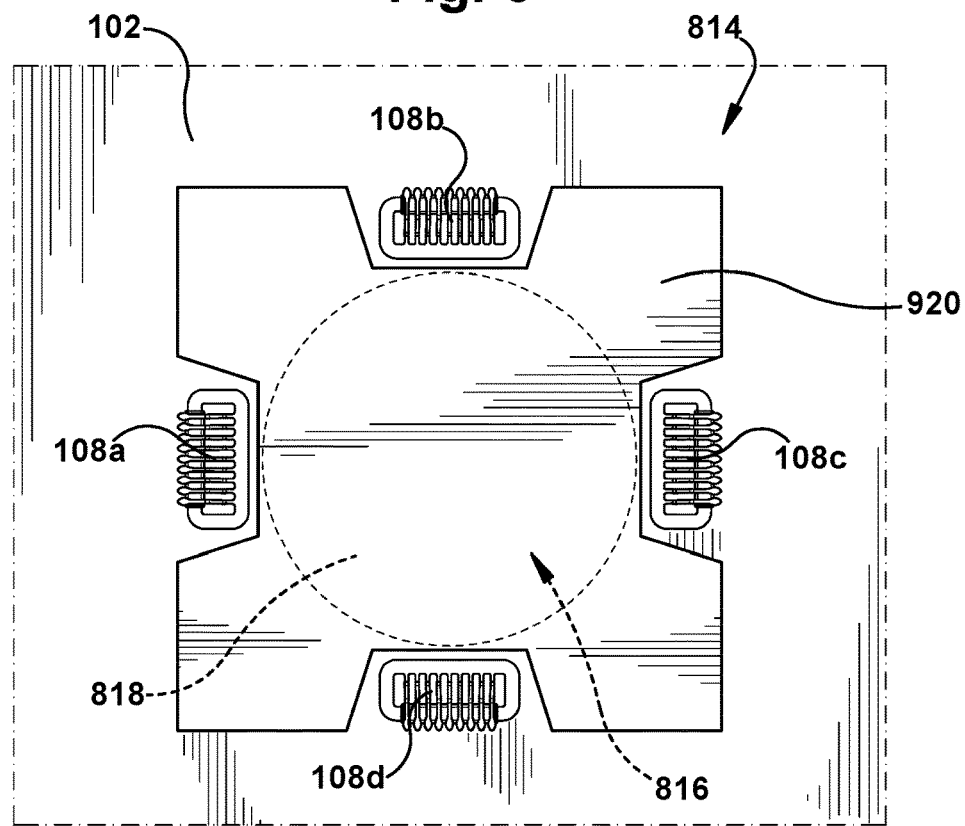
FIG. 7 is a bottom view of a portion of the specialized drape of FIG. 6.
Figure 8:
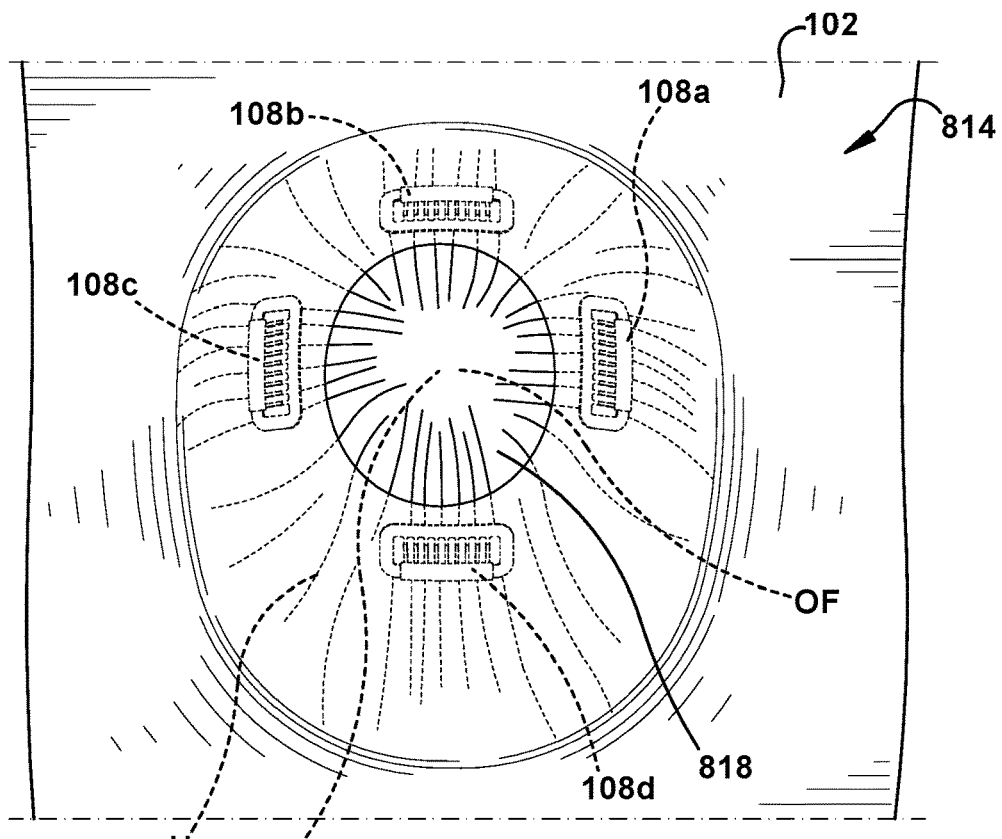
FIGS. 8-9 illustrate an example sequence of operation of a portion of the specialized drape of FIG. 6.
Figure 9:
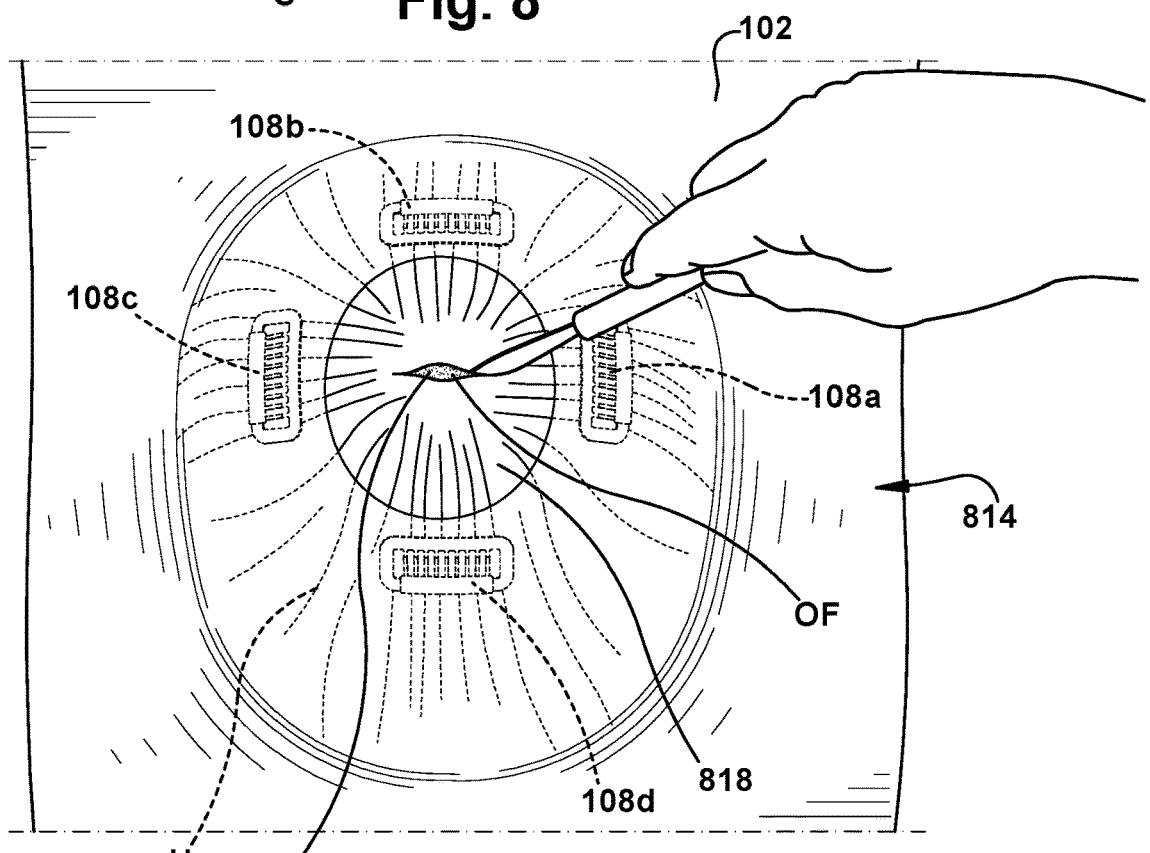

The configuration shown in FIGS. 6-7 is a specialized drape 814 that has a substantially circular configuration. The sheet 102 of the circular specialized drape 814 may include a circular opening 816 that is configured to be placed over an operating field OF. The circular opening may be covered by an incise drape 818. The incise drape 818 may have an adhesive provided thereon so that the incise drape 818 may function as the sealing member 104 when in use. Further, the incise drape 818 may have antimicrobial properties to help keep the operating field sterile. As shown in FIG. 7, a removable protective sheet 920 may cover the adhesive provided on the incise drape 818 prior to use of the circular specialized drape 814. FIG. 8 depicts the circular specialized drape 814 in use with the incise drape 818 provided over an operating field OF. As shown in FIG. 9, once the circular specialized drape 814 is in position, a user may cut through a portion of the incise drape 818 to access the operating field OF.

Figure 10:
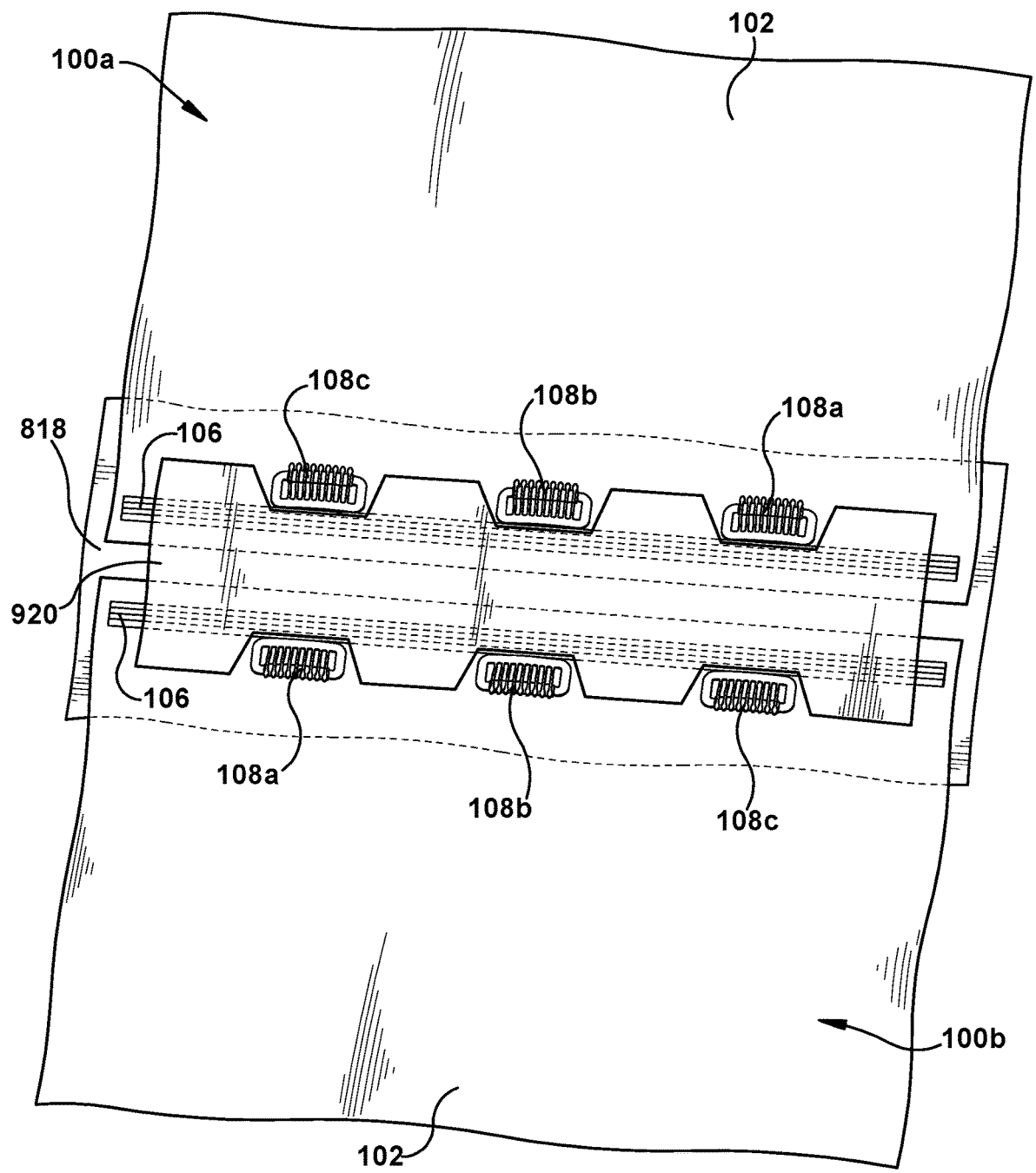
FIG. 10 is a bottom view of the specialized drape of FIG. 1, in another configuration.

The incise drape 818 may also be utilized with the linear specialized drape 100. For example, as shown in FIG. 10, the incise drape 818 may extend between two linear specialized drapes 100 (shown here as linear specialized drapes 100a and 100b). In this configuration, the incise drape 818 may be provided over an operating field OF that is positioned between the two linear specialized drapes 100a, 100b. Further in the configuration shown in FIG. 10, the incise drape 818 may function as a sealing member 104.

Figure 11:
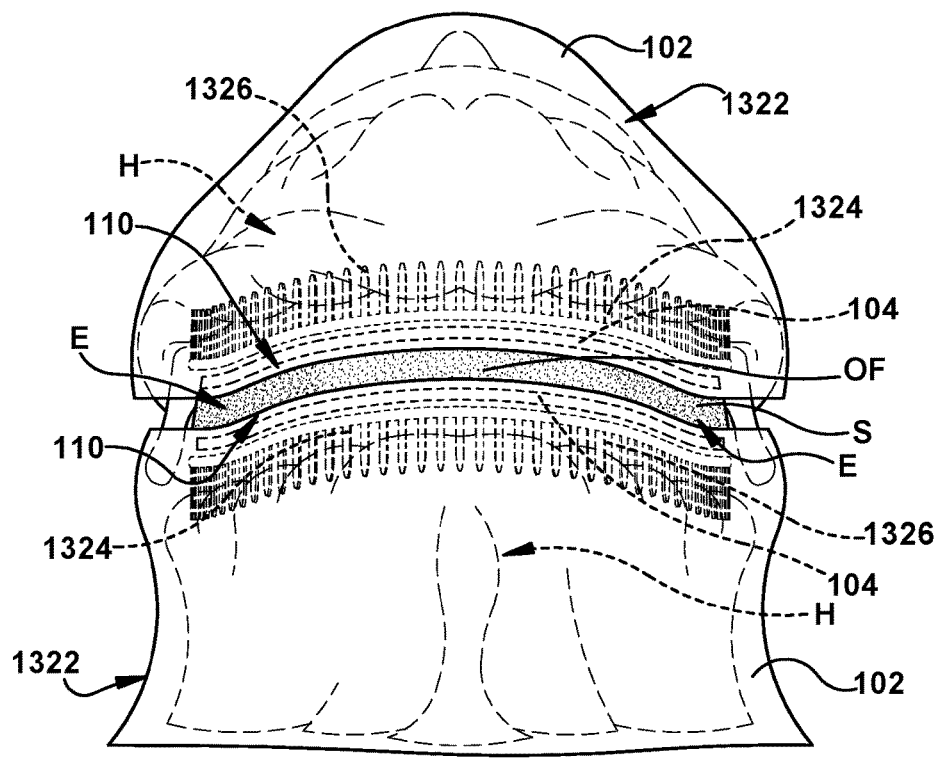
FIG. 11 is a top view of the specialized drape according to a another configuration, and in an example use environment.
Figure 12:
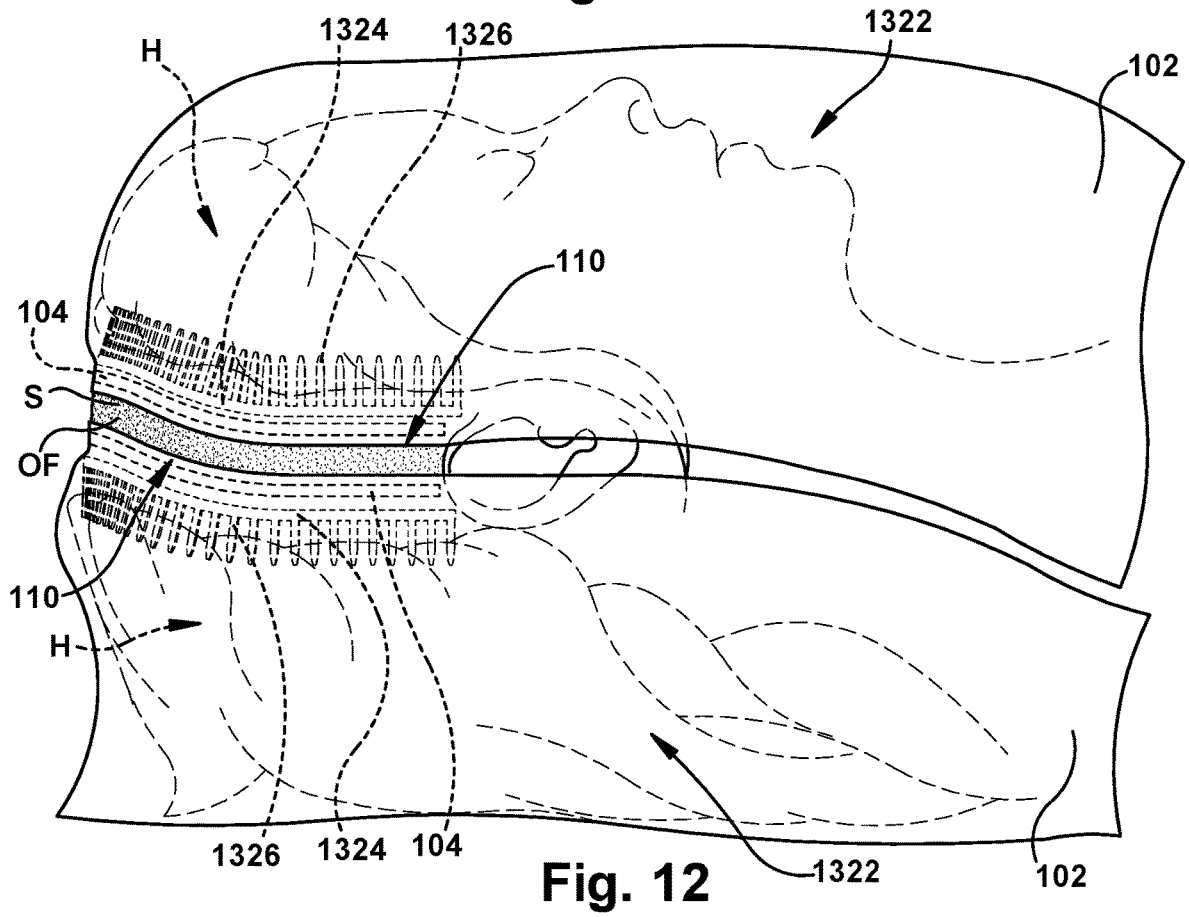
FIG. 12 is a side view of the specialized drape of FIG. 11, in the example use environment.
Figure 13:
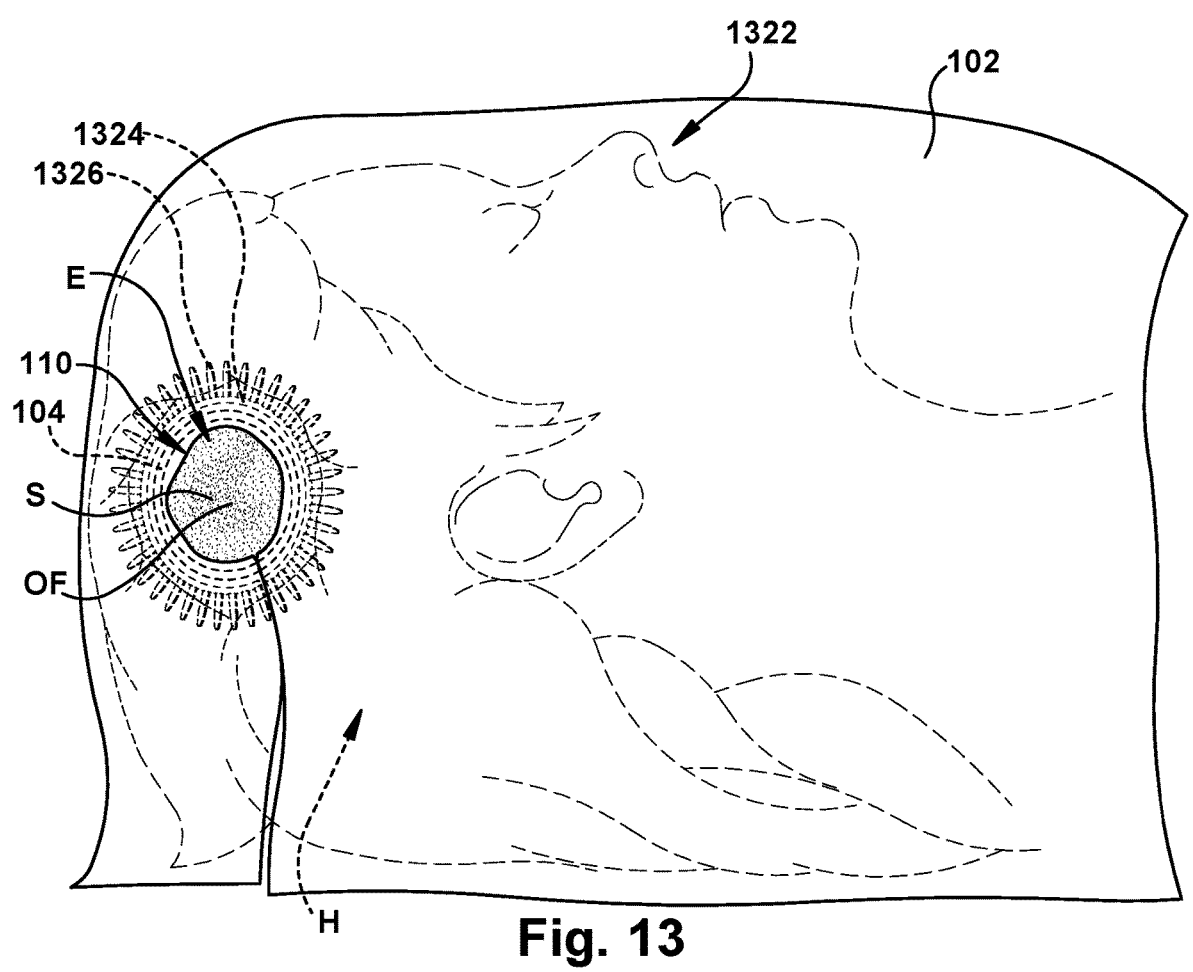
FIG. 13 is a perspective top view of the specialized drape of FIG. 11, in another configuration, and in an example use environment.

FIGS. 11-13 depict another configuration of a specialized drape 1322. Similar to the linear specialized drape shown in FIG. 1, the specialized drape 1322 of FIGS. 11-13 includes a sheet 102, a sealing member 104, and at least one anchoring member 1322. However, unlike the hair-clip anchoring members 108a, 108b, 108c of the linear specialized drape 100 shown in FIG. 1, the anchoring member 1324 of the specialized drape 1322 of FIGS. 11-13 is configured as a comb. The comb anchoring member 1324 has a flexible design that can contour to the patient's head P (FIGS. 11-12) or around circular operating fields OF (FIG. 13). Teeth 1326 of the comb anchoring member 1324 allow the comb anchoring member 1324 to maintain a firm hold in the patient's hair H. The comb anchoring member 1324 may be configured to comb and hold the patient's hair H out of the operating field OF during application of the specialized drape 1322, and thus may function in place of the hair guiding member 106 described above.

In its packaging, the sheet 102 may be folded on top of the comb anchoring member 1324. Further, in its packaging, the sealing member 104 may be protected by the removable protective strip (not shown). To apply the specialized drape 1322 of FIGS. 11-13, a user gently but firmly inserts the comb anchoring member 1324 into the patient's hair H adjacent to an operating field OF. Once the comb anchoring member 1324, and correspondingly the specialized drape 1322, is secured to the patient's hair H, the user peels off the protective strip and presses the sealing member 104 onto a shaved area at an edge E of the operating field OF. The user then unfolds the sheet 102 over the patient's hair H. At this point, all patient hair adjacent to the operating field should be covered by sheet 102 and an appropriate seal has been created along the edges E of the operating field OF (FIGS. 11-13). The operating field OF may now be prepped and disinfected with, for example, betadine or chlorhexidine, and may be draped with standard sterile adhesive drapes according to usual sterile techniques. Alternatively, the specialized drape 1322 may be packaged sterilely and the user may apply the specialized drape 1322 as described above and in a sterile fashion once the designated operating field OF has been shaved and disinfected. At the end of surgery, the specialized drape 1322 is removed and may be discarded or cleaned and sterilized using known techniques.

The sequence of applying the specialized drape 1322 to a patient presented above illustrates just one example sequence of operation. This sequence is not intended to limit the manner in which the specialized drape 1322 is applied to a patient. Any of the steps detailed below can be performed before or after any other step depending on the configuration of the of the specialized drape 1322. For example, when the specialized drape 1322 includes a glue-based sealing member 104, it may be desirable to apply the glue-based sealing member 104 to the patient's skin S before attaching the rest of the specialized drape 1322 in the manner described above.

The specialized drape 1322 of FIGS. 11-13 may have multiple shapes and sizes available that are customizable to different procedures. A longer, larger sheet 102 with a comb anchoring member 1324 having wider teeth 1326 may be particularly appropriate for bicoronal incisions that extend from one ear to the other over the top of the scalp (FIGS. 11-12). A more rounded comb anchoring member 1324 with shorter teeth 1326 may be particularly well suited for being placed around the circumference of a small incision and/or a small operating field OF for excision of a 1-2 cm lesion of the scalp (FIG. 13). Many combinations of anchoring member 1324 and sheet 102 size and shape are possible based on incision requirements for different procedures.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Further, the chosen material(s) may have anti-microbial properties to help keep an operating field sterile. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for protecting an operating field, comprising:
   a sheet configured to cover at least a portion of a patient's hair during an operation;
   an adhesive portion with an adhesive strip portion, wherein the adhesive strip portion is incorporated within, provided on, or attached to the sheet, the adhesive strip portion configured to create a barrier to keep the patient's hair away from the operating field; and
   at least one anchoring member connected to the sheet, the at least one anchoring member being configured to be attached to the patient's hair to anchor the apparatus to the patient.

2. The apparatus of claim 1, wherein the at least one anchoring member is a flexible comb that is configured to at least partially contour to a patient's head or flex into a circular configuration around a circular operating field.

3. The apparatus of claim 1, further comprising an incise drape, wherein the incise drape is configured to be placed over the operating field.

4. The apparatus of claim 3, wherein the incise drape comprises an incise drape adhesive, wherein the incise drape adhesive is configured to be adhered to a patient's skin.

5. The apparatus of claim 1, wherein the adhesive strip portion is an uninterrupted strip of adhesive.

6. The apparatus of claim 1, wherein the at least one anchoring member is at least one of a hair clip, a comb, and a hairpin.

7. The apparatus of claim 1, wherein the at least one anchoring member is a plurality of hair clips.

8. The apparatus of claim 1, wherein a leading edge portion surrounds a circular opening in the sheet, wherein the circular opening is configured to provide access to the operating field.

9. The apparatus of claim 1, wherein a leading edge portion of the apparatus surrounds a semi-circular opening in the sheet, wherein the semi-circular opening is configured to provide access to the operating field.

10. The apparatus of claim 1, wherein the adhesive strip portion is at a leading edge portion of the sheet.

* * * * *